United States Patent
Holden et al.

(10) Patent No.: US 7,969,568 B2
(45) Date of Patent: Jun. 28, 2011

(54) SPECTROGRAPHIC METROLOGY OF PATTERNED WAFERS

(75) Inventors: James Matthew Holden, San Jose, CA (US); Edgar Genio, Santa Clara, CA (US); Todd J. Egan, Fremont, CA (US)

(73) Assignee: Applied Materials, Inc., Santa Clara, CA (US)

( * ) Notice: Subject to any disclaimer, the term of this patent is extended or adjusted under 35 U.S.C. 154(b) by 341 days.

(21) Appl. No.: 12/369,627

(22) Filed: Feb. 11, 2009

(65) Prior Publication Data

US 2010/0103411 A1    Apr. 29, 2010

Related U.S. Application Data

(60) Provisional application No. 61/197,270, filed on Oct. 24, 2008.

(51) Int. Cl.
*G01J 3/00* (2006.01)

(52) U.S. Cl. .......................... 356/300; 382/145

(58) Field of Classification Search ............ 356/300; 382/145

See application file for complete search history.

(56) References Cited

U.S. PATENT DOCUMENTS

| | | | |
|---|---|---|---|
| 5,834,203 A * | 11/1998 | Katzir et al. | 435/6 |
| 6,640,014 B1 | 10/2003 | Price et al. | 382/255 |
| 6,974,963 B2 * | 12/2005 | Tanaka et al. | 356/394 |
| 7,245,412 B2 | 7/2007 | Bruland et al. | 359/225 |
| 2002/0054704 A1* | 5/2002 | Smilansky et al. | 382/149 |
| 2002/0108892 A1* | 8/2002 | Goetz et al. | 209/576 |
| 2004/0246493 A1 | 12/2004 | Kim et al. | 356/507 |
| 2005/0046850 A1* | 3/2005 | Chow | 356/430 |
| 2007/0229852 A1* | 10/2007 | Wack et al. | 356/625 |

* cited by examiner

*Primary Examiner* — Kara E Geisel (74) *Attorney, Agent, or Firm* — Robert M. Wallace (57) ABSTRACT

Light reflected from respective image elements of a workpiece is channeled through respective light channeling elements to respective locations of a spectrographic light disperser. Spectral distributions of the respective image elements produced by the spectrographic light disperser are recorded. A processor groups similar spectral distributions into respective groups of mutually similar distributions, and classifies the groups by the number of distributions contained in each group.

20 Claims, 8 Drawing Sheets

SPECTROGRAPHIC METROLOGY OF PATTERNED WAFERS

CROSS-REFERENCE TO RELATED APPLICATIONS

This application claims the benefit of U.S. Provisional Application Ser. No. 61/197,270, filed Oct. 24, 2008 entitled SPECTROGRAPHIC METROLOGY OF PATTERNED WAFERS, by James Matthew Holden, et al.

BACKGROUND

Fabrication of thin film products such as microelectronic integrated circuits is enhanced by periodic measurements of key characteristics of the product during the fabrication process, enabling on-going process adjustments to enhance quality and yield. Characteristics of interest include film thickness, feature spacing, feature size or critical dimension at or around a specific location or a specific circuit element. Measurements of such characteristics are best made by analyzing the wavelength spectrum of light reflected from the feature or location of interest on the workpiece or wafer. How to infer a measurement of such characteristics from the wavelength spectrum is known, and may use a conventional technique such as rigorously coupled wave analysis, for example. Many measurements may be desired during the processing of each individual wafer, so that the time required to perform each measurement reduces productivity. Each measurement typically requires a significant amount of time, during which the wafer cannot be processed and instead is held in a metrology tool. Moreover, the wafer and metrology optics must be carefully positioned to ensure that the measurement is taken in a homogeneous region of the integrated circuit, within which the characteristic to be measured (e.g., thin film thickness, step height, etc.) is the same across the entire region. There is a need to perform such measurements without detracting from productivity.

SUMMARY

A method of performing on-the-fly spectrographic metrology of a workpiece is provided. An optical sensor is provided having a field of view coinciding with a path traversed by the workpiece during transfer in a workpiece handling apparatus, and a still image of the workpiece is obtained through the sensor during transfer of the workpiece along the path. Light reflected from respective image elements of the image is channeled through respective light channeling elements to respective locations of a spectrographic light disperser. Spectral distributions of the respective image elements produced by the spectrographic light disperser are recorded. A processor searches for spectral distributions that are similar to one another and groups the distributions into groups of mutually similar distributions. The groups are classified by the number of distributions contained in each group. The largest group is selected and its distributions are combined together to provide and enhanced distribution for processing in accordance with a spectral analysis process. The enhanced spectral distribution represents a single homogeneous region of the workpiece.

BRIEF DESCRIPTION OF THE DRAWINGS

So that the manner in which the exemplary embodiments of the present invention are attained and can be understood in detail, a more particular description of the invention, briefly summarized above, may be had by reference to the embodiments thereof which are illustrated in the appended drawings. It is to be appreciated that certain well known processes are not discussed herein in order to not obscure the invention.

To facilitate understanding, identical reference numerals have been used, where possible, to designate identical elements that are common to the figures. It is contemplated that elements and features of one embodiment may be beneficially incorporated in other embodiments without further recitation. It is to be noted, however, that the appended drawings illustrate only exemplary embodiments of this invention and are therefore not to be considered limiting of its scope, for the invention may admit to other equally effective embodiments.

DETAILED DESCRIPTION

Figure 1:
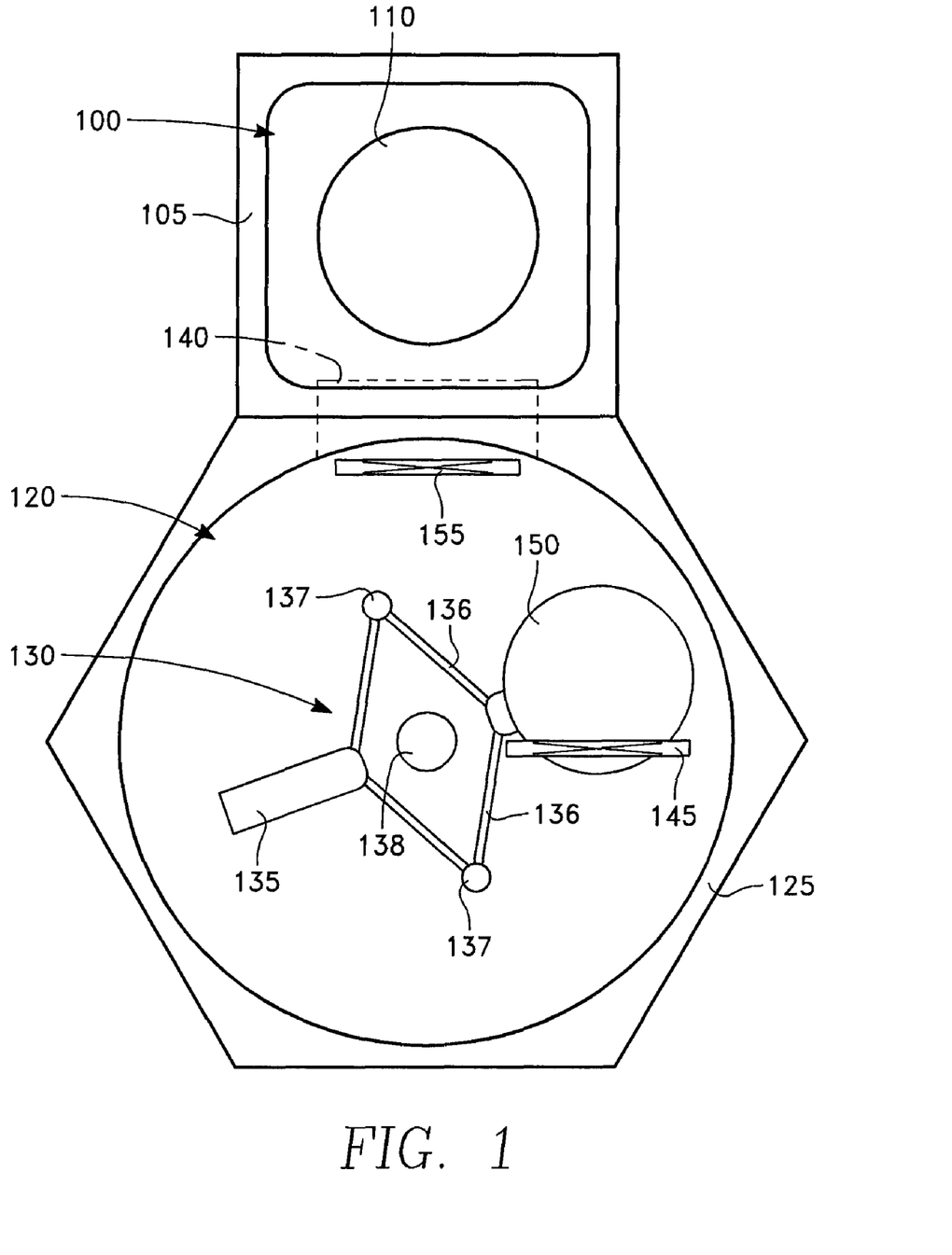
FIG. 1 is a top view of a workpiece transfer apparatus in accordance with one embodiment.

FIG. 1 depicts apparatus in accordance with one embodiment. A plasma reactor chamber 100 has a chamber side wall 105 and a wafer support pedestal 110 for supporting a wafer or workpiece during processing. A wafer transfer station 120 adjacent the chamber 100 has a side wall 125 and contains a robotic wafer handler 130 including an arm 135, the robotic handler 130 and arm 135 being of a conventional type. For example, the handler 130 may include extension rods 136 joined at extension joints 137 and a center axle 138, the arm 135 being rotatable about the axle 138 and being radially extendable by movement of the rods 136. A passage way or slit valve 140 permits wafer transfer between the transfer station 120 and the chamber 100. Transfer station 120 may be in communication with or be integrated within a factory interface (not shown). During operation, a wafer may be received by the arm 135 from an external source (such as a factory interface) and transported in an arcuate path by the arm 135. A metrology sensor 145 may overlie a wafer location 150 occupied by the wafer at some instant while the arm 135 rotates about the center axle 138. Another metrology sensor 155 may overlie a portion of the path traveled by the wafer as the arm 135 inserts the wafer through the slit valve or passage 140. Each sensor 145, 155 contains a strobe light source for capturing spectrographic samples of the wafer on the fly as the wafer is transported by the robotic handler 130, so that productivity is not affected by wafer metrology. Performing metrology on the fly in this manner has not been practical because the location of the image within the wafer cannot be ascertained instantly, so that the sampled image cannot be properly interpreted. For example, a single image (or spectrum) captured by the strobe light may include different regions of an integrated circuit having entirely different values of the characteristic (e.g., film thickness, step height, etc.) being measured. In such a case, the sample would be an average between the two regions captured in the instantaneous sample, so that the true characteristic value in either region would be lost. How this problem is solved is described later in this specification.

Figure 2:
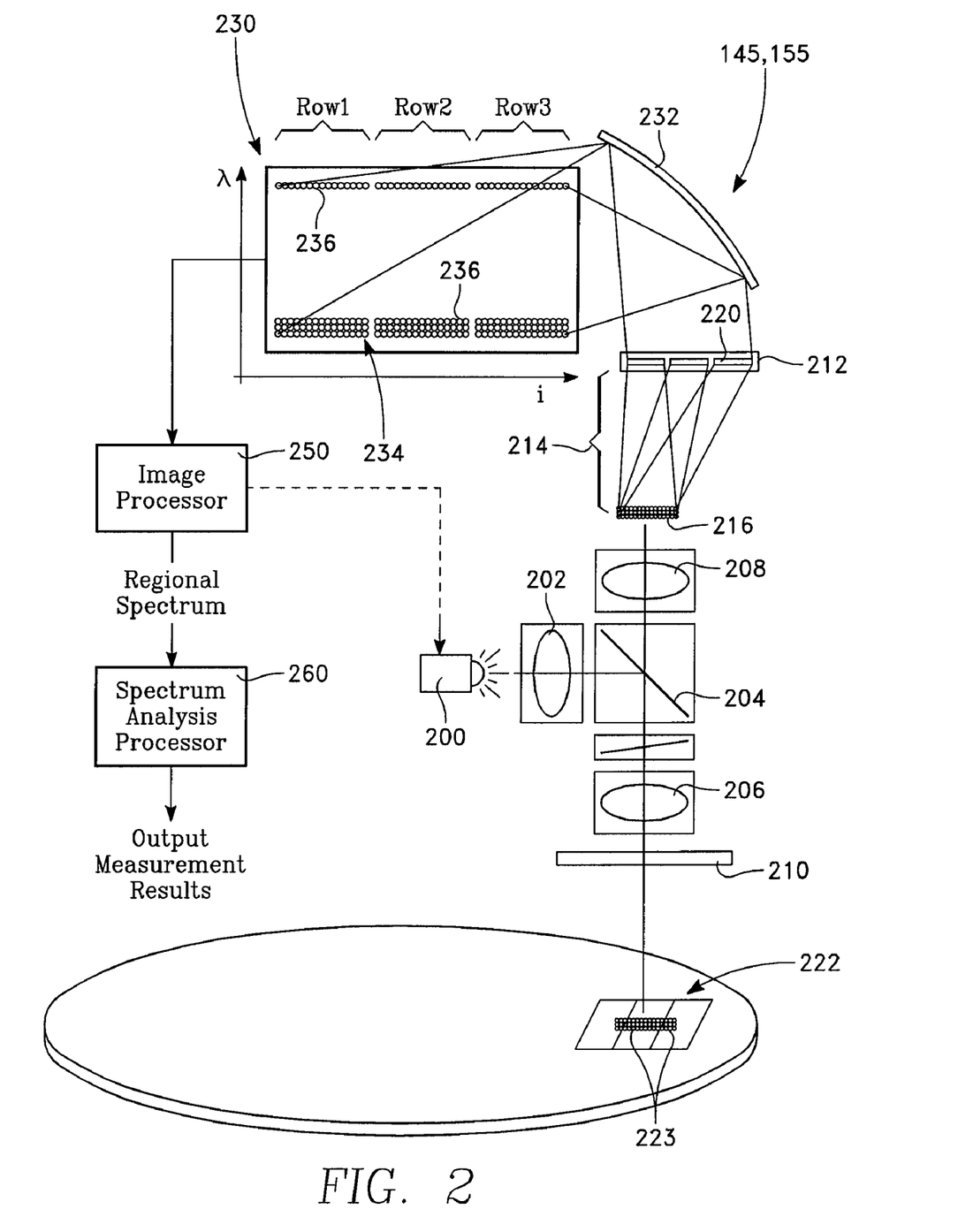
FIG. 2 depicts an optical system of a sensor employed in the apparatus of FIG. 1.

FIG. 2 depicts the components of the sensor 145 or 155 in relation to the wafer being measured. The sensor includes a strobe lamp 200, a strobe lens 202, a beam splitter 204, a gathering lens 206, a collimating lens 208 and a window 210. The sensor further includes a wavelength dispersing element 212 which may be a spectrographic diffraction grating or a prism. An array 214 of light channeling elements 216 map individual image elements (pixels) of the image formed by the lens 208 to respective locations along a linear slit 220 of the diffraction grating 212. As will be described below, the array 214 of light channeling elements 216 may implemented in various ways, such as a bundle of fiber optic cables (in which case each channeling element 216 is an optical fiber) or an array of micro lenses (in which case each channeling element 216 is a micro lens). In the embodiment illustrated in FIG. 2, the light channeling element array 214 maps a two-dimensional image 222 consisting of an array of image elements 223 from the wafer into an ordered line of image elements along the diffraction grating slit 220. Each image element 223 is captured by a corresponding one of the light channeling elements 216.

An imager such as a charge coupled device (CCD) array 230 captures the spectrographic images formed by the diffraction grating 212. A lens assembly represented as a lens 232 focuses the light from the diffraction grating 212 onto the imager array 230. The image on the array 230 is ordered in columns 234 of pixels 236 in accordance with a column index number i, each column 234 being formed from the light of a respective one of the light channeling elements 216. As indicated in FIG. 2, the individual pixels 236 of each column 234 are aligned in order of increasing wavelength, λ. Thus, each image element 223 in the captured wafer image 222 is mapped to a column 234 of pixels 236 on the imager 230, each column 234 constituting a spectrographic image of one image element 223. In the embodiment of FIG. 2, there are three rows of light channeling elements 216 in the array 214 (labeled ROW 1, ROW 2 and ROW 3) facing the lens 208, and the lens assembly 232 focuses the light such that the three rows are ordered in sequence from left to right across imager 230, each image element 223 being mapped to a wavelength dispersed column on the imager 230. The image data held in the imager array 230 is furnished to an image processor 250. The processor 250 deduces from the data which ones of the light channeling elements 216 are aligned exclusively over a homogeneous region of interest of the wafer, and combines their outputs to produce an enhanced spectrum. A spectrum analysis processor 260 analyzes the enhanced spectrum to provide a measurement of a characteristic (e.g., film thickness) of that homogeneous region of the integrated circuit.

Figure 3A:
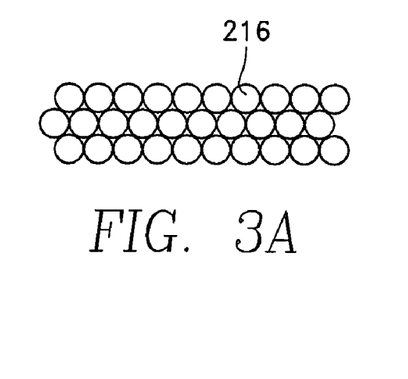
FIGS. 3A and 3B depict respective embodiments of an array of light channeling elements in the system of FIG. 2.
Figure 3B:
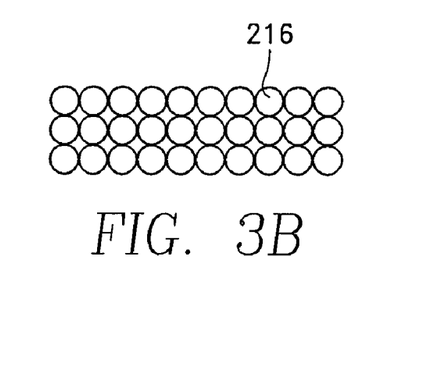
Figure 10A:
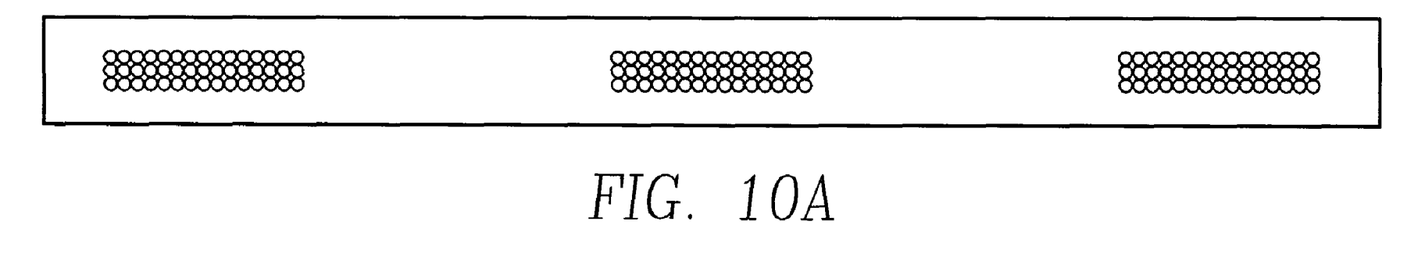
FIGS. 10A and 10B depict respective embodiments a sensor including light channeling elements.
Figure 10B:
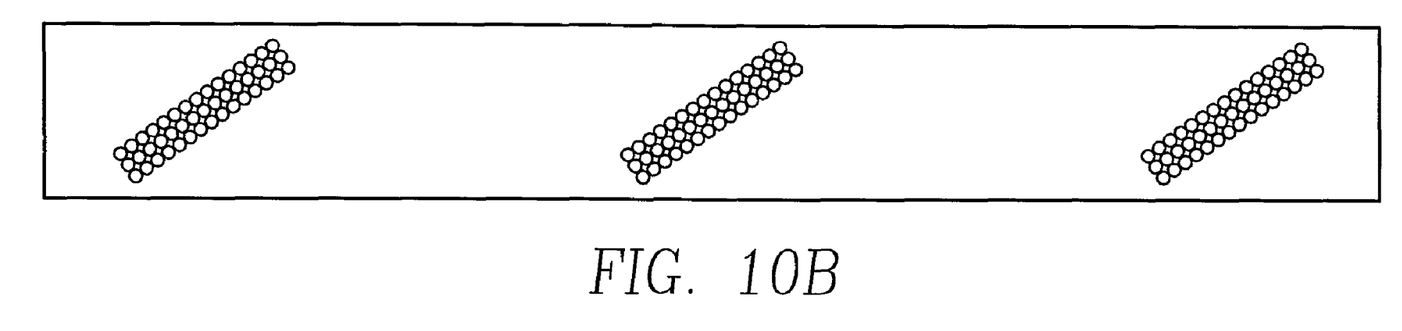

FIGS. 3A and 3B depict alternative arrangements of the light channeling elements 216 at the plane nearest the wafer, in which the channeling elements are either interdigitated (FIG. 10A) or in registration (FIG. 10B). In either case, the channeling elements 216 are closely packed to minimize the empty voids between them.

Figure 4:
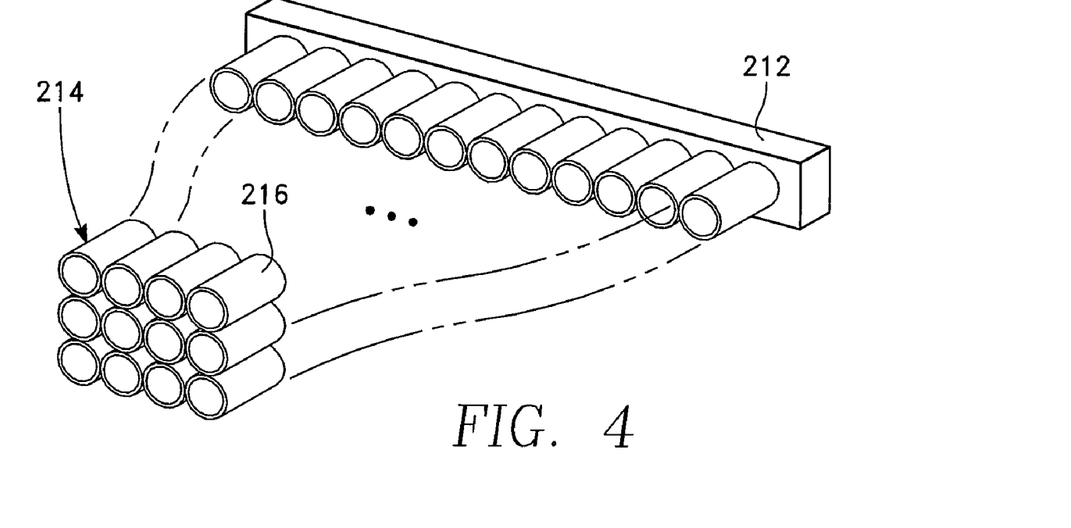
FIG. 4 depicts an array of light channeling elements in accordance with an embodiment employing optical fibers.
Figure 5:
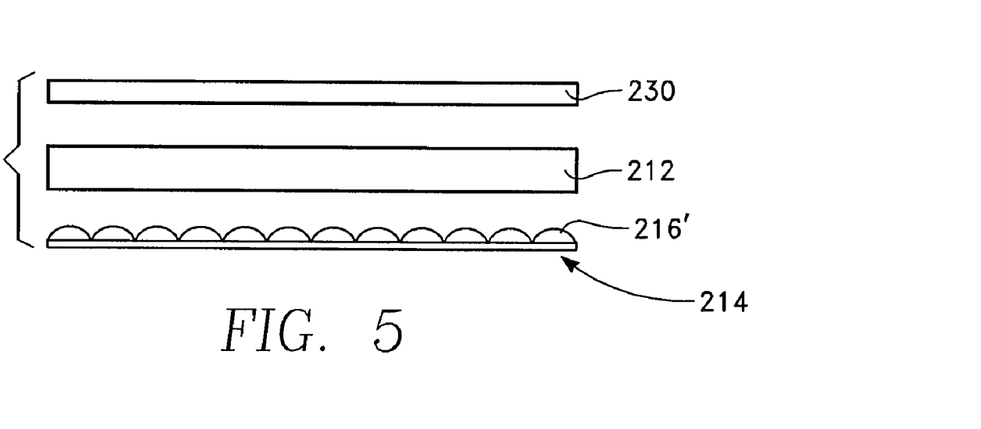
FIG. 5 depicts an array of light channeling elements employing micro-mirrors.

FIG. 4 depicts the array 214 of light channeling elements 216 as a fiber optic bundle. At the end facing the wafer, the fiber optic bundle forms a two-dimensional array of fiber ends, while at the end facing the diffraction grating 212, the fiber optic bundle is flattened to form a single line of fiber-optic ends. FIG. 5 depicts an alternative embodiment of the array 214 in which each light channeling element 216' is a micro lens. The individual lenses may be oriented to transform the two-dimensional image captured from the wafer into a linear sequence of image elements along the diffraction grating 212.

Figure 6:
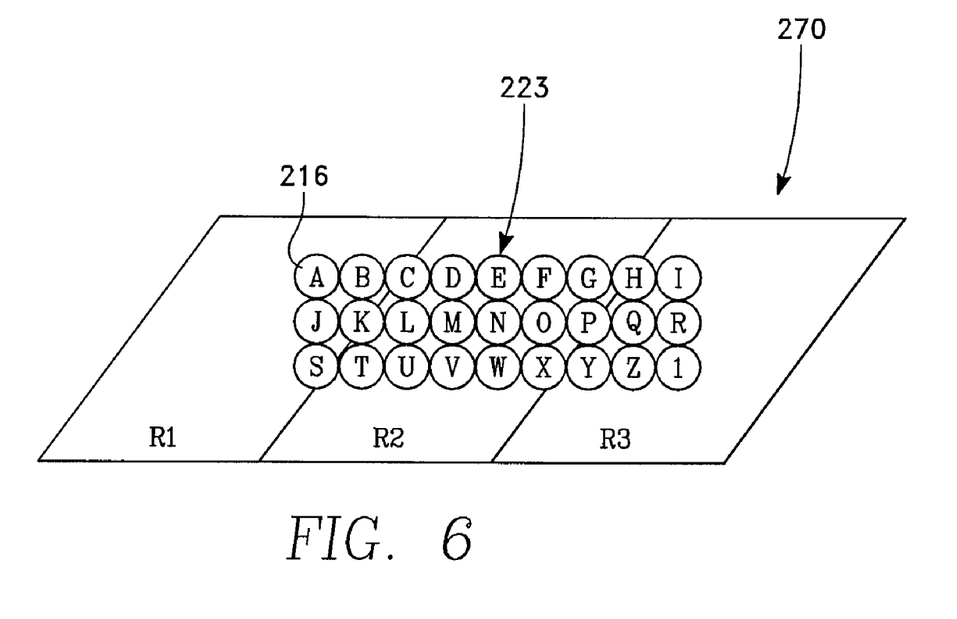
FIG. 6 depicts the light channeling elements overlying different regions of a workpiece.
Figure 7:
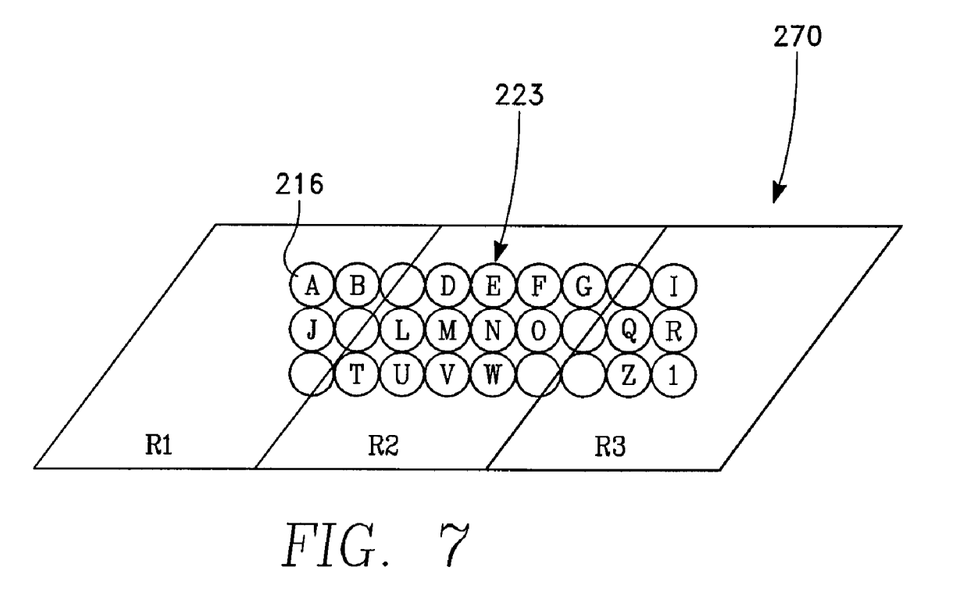
FIG. 7 conceptually depicts suppression of output of certain light channeling elements in accordance with an embodiment.

FIG. 6 is an enlarged view of a portion of FIG. 2, depicting the location on a wafer surface 270 of each image element 223 captured by a corresponding light channeling element 216. The image elements 223 are labeled A through Z. The integrated circuit topology on the wafer surface within the field of view defined by the array of image elements 223 may consist of three different regions, labeled R1, R2 and R 3 in FIG. 6. For example, the region R1 may be a memory array, the region R2 may be a logic array and the region R3 may be an unpatterned area. The structural features of these different areas will naturally differ. For example, the thickness of the top thin film will be different in each of these areas. In this example, the spectra obtained from different ones of the channeling elements 216 will reflect the film thickness of a different region, and some of the spectra will be corrupted by light from adjacent regions and therefore be misleading. FIG. 6 depicts a goal in accordance with one embodiment, which is to reject information from those channeling elements 216 that receive light from any image element that overlies two adjacent regions. In the illustrated example of FIG. 7, the rejected image elements are H, P, X and Y between regions R2 and R3, and C, K and S between regions R1 and R2. A further goal is to associate the image elements of the same region. In the example of FIG. 6, the image elements A, B, J and S should be associated together with region R1, the image elements D-G, L-O and T-W should be associated together with region R2, and the image elements I, Q, R, Z and 1 should be associated together with region R3. The problem is how to perform such filtering and grouping in an image which is attained on the fly using an instantaneous strobe light source.

Figure 8A:
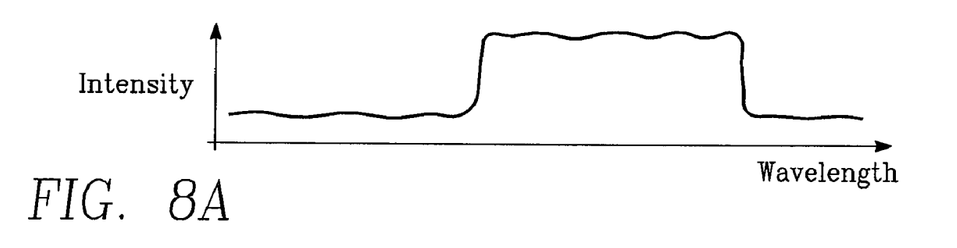
FIGS. 8A through 8E are graphs of spectral distributions from different light channeling elements of FIG. 2, the ordinate of each graph representing intensity and the abscissa representing wavelength.
Figure 8B:
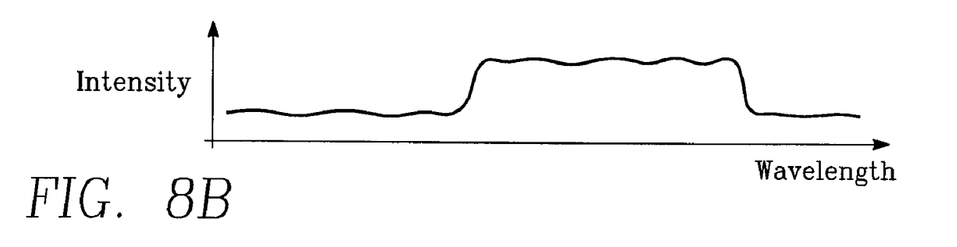
Figure 8C:
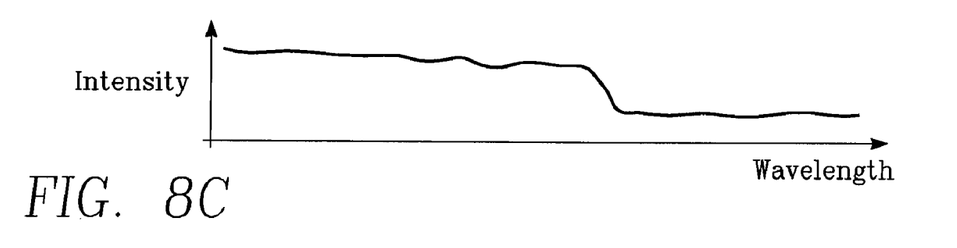
Figure 8D:
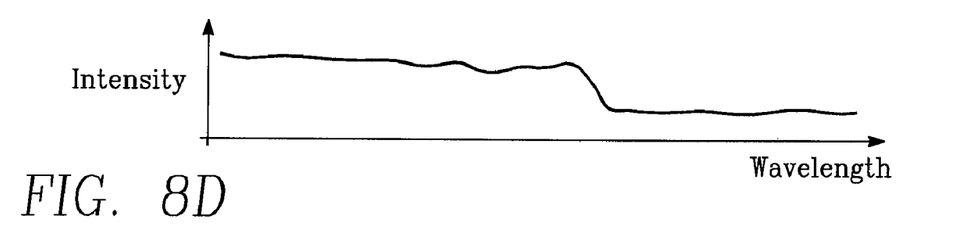
Figure 8E:
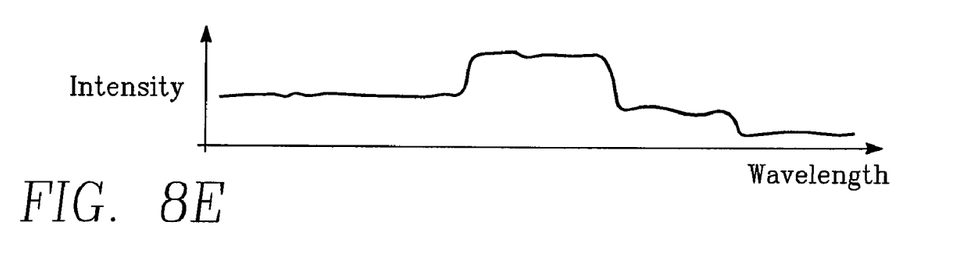

This problem is solved by processing the individual spectra of all the image elements 223 in the image processor 250. The processor 250 may receive a set of spectra depicted in FIGS. 8A through 8E. Each individual spectrum is represented by the data (image intensities) stored in an individual column 234 of the sensor 230 of FIG. 2. The spectra from image elements 223 lying in the same region are at least approximately the same. The spectra from image elements 223 lying in different regions differ significantly from one another. For example, FIGS. 8A and 8B represent spectra from the image elements A and J lying in the same region, R1, FIGS. 8C and 8D represent spectra from the image elements D and M lying in the same region, R2, and FIG. 8E represents the spectra from the image element K that overlies both adjacent regions R1 and R2. From FIG. 6, it is apparent that there will be a relatively large number of image elements 223 having spectra nearly the same as that of FIGS. 8C and 8D, namely image elements D-G, L-O and T-W. A smaller number of image elements will have spectra nearly the same as FIGS. 8A and 8B, namely image elements A, B and J. However, the spectra of image elements C, K and S that straddle the two regions R1 and R2 have different spectra, like that of FIG. 8E. The spectra of image elements C, K and S will each differ from one another because they are each distributed over the two regions R1 and R2 differently. The processor 250 groups the spectra by similarity. The spectra of image elements D-G, L-O and T-W are put into a first group, and the spectra of A, B and J are put into a second group. However, the spectra of C, K and S are not put into any group because none of them is sufficiently similar to any other spectra. The processor 250 clearly may pick the largest group (D-G, L-O and T-W) as a valid set of spectra from the same homogeneous region of the integrated circuit. Since this is the largest group, it clearly corresponds to the region over which the sensor is most centered, and may therefore be identified. The spectra of this group may be added together to enhance signal-to-noise ratio, and the enhanced spectrum may be processed by the spectrum analysis processor 160 to measure the characteristic of interest (e.g., film thickness, step height, etc.).

Figure 9:
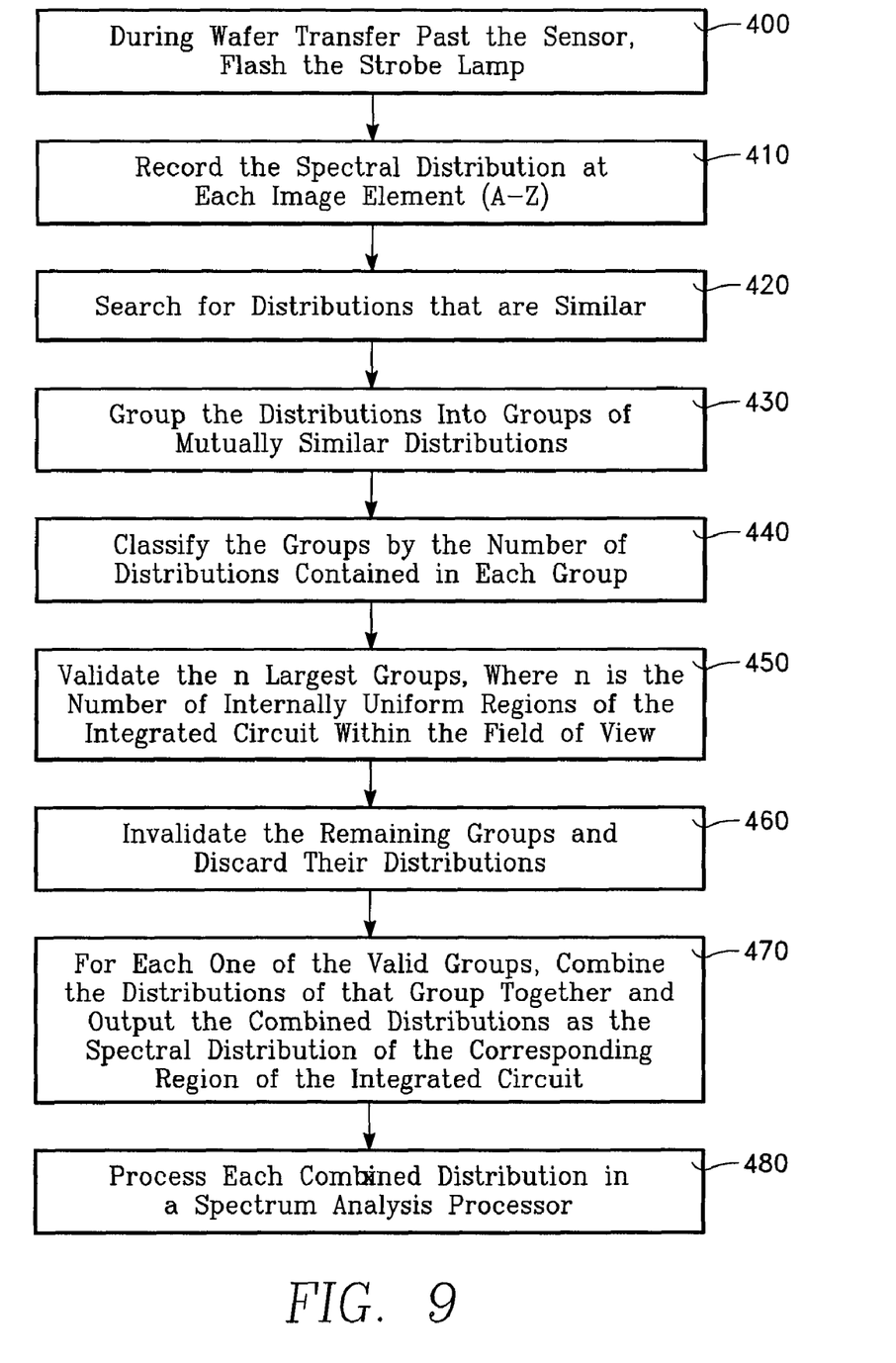
FIG. 9 is a flow diagram of a process in accordance with one embodiment.

One embodiment of such a process is depicted in FIG. 9. This embodiment may be carried out as follows: during wafer transfer past the sensor, the strobe lamp is flashed once (block 400 of FIG. 9). The resulting spectral distribution at each image element is recorded (block 410 of FIG. 9). Every pair of distributions is compared to determine whether they are similar (block 420 of FIG. 9). The determination of similarity may be based upon conventional calculations, such as mean square error, sum of absolute differences or sum of variances. The processor then groups the distributions into groups of mutually similar distributions (block 430 of FIG. 9). The next step is to classify the groups by the number of distributions contained in each group (block 440 of FIG. 9), and validate the n largest groups, where n is the number of internally uniform regions of the integrated circuit within the field of view, or a number less than that (block 450). In one embodiment, existence of similarity between any two distributions may be inferred in block 430 whenever the sum of the variances between them is less than a predetermined threshold. This predetermined threshold may be varied in a trial and error procedure until the number of groups, n, found in block 430 matches the number of homogeneous regions within the field of view of the sensor. The processor invalidates the groups not validated in block 450 and discards their distributions (block 460). This step corresponds to the drawing of FIG. 7, in which certain ones of the image elements are shown as blank. For each one of the valid groups, the processor combines the distributions of that group together and outputs the combined distribution as the spectral distribution of the corresponding region of the integrated circuit (block 470). The spectrum analysis processor 270 processes each combined distribution in accordance with a conventional spectrum analysis process (block 480 of FIG. 9).

FIG. 10A illustrates how the light channeling elements 216 may be oriented in a rectangular fashion in plural groups, while FIG. 10B illustrates how the light channeling elements 216 may be oriented in a diagonal fashion.

Figure 11:
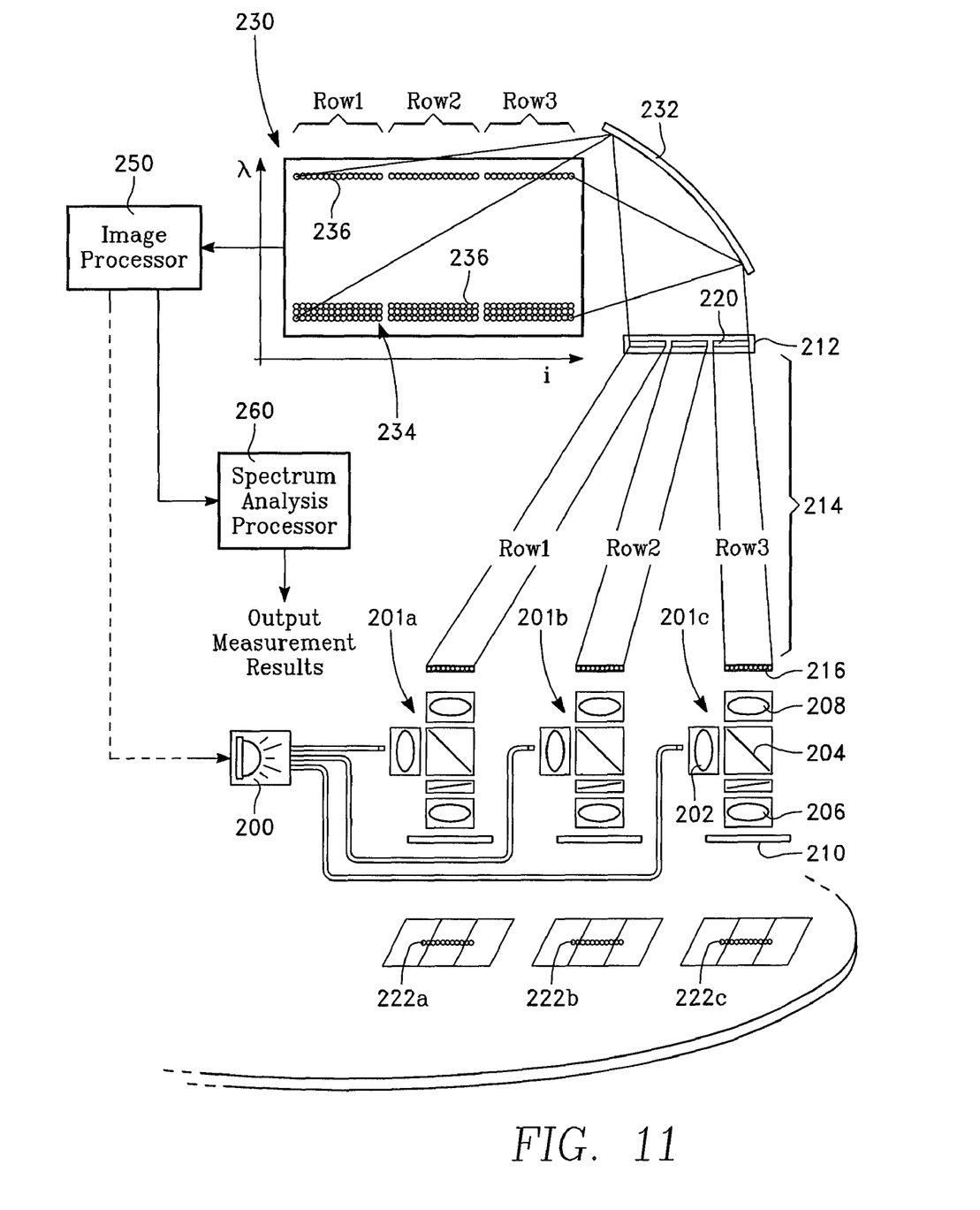
FIG. 11 depicts an optical system for a sensor viewing different regions of a workpiece that may be employed in the apparatus of FIG. 1.

FIG. 11 illustrates a modification of FIG. 2 in which the different rows of light channeling elements 216 (Row 1, Row 2 and Row 3) are separately coupled to different sets of optics 201a, 201b, 201c, respectively. Each one of the optics 201a, 201b, 201c consists of an individual set of the optical elements 202, 204, 206, 208, 210 described above with reference to FIG. 2. The optics 201a, 201b, 201c are positioned over different locations of the wafer, to capture separate images 222a, 222b, 222c, respectively. A common strobe light 200 illuminates the optics 201a, 201b, and 201c. The embodiment of FIG. 11 can be used to make simultaneous measurements in different widely spaced zones of the wafer.

While the foregoing is directed to embodiments of the present invention, other and further embodiments of the invention may be devised without departing from the basic scope thereof, and the scope thereof is determined by the claims that follow.

What is claimed is:

1. In a workpiece handling chamber, a method of performing on-the-fly spectrographic metrology of a workpiece, comprising:
providing an optical sensor having a field of view coinciding with a path traversed by the workpiece during transfer in the workpiece handling apparatus, and obtaining a still image of the workpiece through said sensor during transfer of said workpiece along said path;
channeling light reflected from respective image elements of said image through respective light channeling elements to respective locations of a spectrographic light disperser;
recording spectral distributions of the respective image elements produced by said spectrographic light disperser;
searching for distributions that are similar to one another and grouping the distributions into groups of mutually similar distributions;
classifying the groups by the number of distributions contained in each group;
selecting at least one of the largest groups and combining the distributions of that group together and providing the combined distribution as the spectral distribution of one region of the integrated circuit; and
processing the combined distribution in accordance with a spectrum analysis process.

2. The method of claim 1 wherein said searching comprises computing a measure of similarity between pairs of said distributions.

3. The method of claim 2 wherein said measure of similarity is one of mean square error, sum of absolute differences, or sum of variances.

4. The method of claim 1 wherein said selecting comprises validating the n largest groups, wherein n is an integer.

5. The method of claim 4 wherein n is at least the approximate number of homogeneous regions of the integrated circuit within a field of view of the sensor.

6. The method of claim 4 further comprising producing an enhanced distribution for each one of said n groups.

7. The method of claim 4 further comprising discarding the distributions of the remaining groups.

8. The method of claim 1 wherein said channeling channels the light to respective locations along a linear slit of said spectrographic light disperser.

9. The method of claim 5 wherein said selecting comprises selecting the largest one of said groups.

10. The method of claim 1 wherein said recording comprises capturing said distributions on a sensor array wherein each said image element corresponds to a column on said sensor array and each wavelength of each distribution corresponds to a row of the respective column.

11. In a workpiece handling chamber, a method of performing spectrographic metrology of a workpiece, comprising:
channeling light reflected from respective image elements on the workpiece through respective light channeling elements to respective locations of a spectrographic light disperser;
recording spectral distributions of the respective image elements produced by said spectrographic light disperser;

searching for distributions that are similar to one another and grouping the distributions into groups of mutually similar distributions;

classifying the groups by the number of distributions contained in each group;

selecting at least one of the largest groups and combining the distributions of that group together and providing the combined distribution as the spectral distribution of one region of the integrated circuit; and processing the combined distribution in accordance with a spectrum analysis process.

12. The method of claim 11 wherein said searching comprises computing a measure of similarity between pairs of said distributions.

13. The method of claim 12 wherein said measure of similarity is one of mean square error, sum of absolute differences, or sum of variances.

14. The method of claim 11 wherein said selecting comprises validating the n largest groups, wherein n is an integer.

15. The method of claim 14 wherein n is at least the approximate number of homogeneous regions of the integrated circuit within a field of view of the sensor.

16. The method of claim 14 further comprising producing an enhanced distribution for each one of said n groups.

17. The method of claim 14 further comprising discarding the distributions of the remaining groups.

18. The method of claim 11 wherein said channeling channels the light to respective locations along a linear slit of said spectrographic light disperser.

19. The method of claim 11 wherein said selecting comprises selecting the largest one of said groups.

20. The method of claim 11 wherein said recording comprises capturing said distributions on a sensor array wherein each said image element corresponds to a column on said sensor array and each wavelength of each distribution corresponds to a row of the respective column.

* * * * *